(12) United States Patent
Poon et al.

(10) Patent No.: US 10,064,544 B2
(45) Date of Patent: Sep. 4, 2018

(54) ENDOSCOPIC CAPSULE AND ENDOSCOPIC SYSTEM

(71) Applicant: The Chinese University of Hong Kong, Hong Kong (CN)

(72) Inventors: Carmen Chung Yan Poon, Hong Kong (CN); Hin Kwong Leung, Hong Kong (CN); RuiKai Zhang, Shenzhen (CN); Cecilia Ka Wing Chan, Hong Kong (CN)

(73) Assignee: THE CHINESE UNIVERSITY OF HONG KONG, Hong Kong (CN)

( * ) Notice: Subject to any disclaimer, the term of this patent is extended or adjusted under 35 U.S.C. 154(b) by 17 days.

(21) Appl. No.: 15/005,263

(22) Filed: Jan. 25, 2016

(65) Prior Publication Data

US 2016/0213234 A1    Jul. 28, 2016

Related U.S. Application Data

(60) Provisional application No. 62/107,760, filed on Jan. 26, 2015.

(51) Int. Cl.
| | | |
|---|---|---|
| *A61B 1/00* | (2006.01) | |
| *A61B 1/04* | (2006.01) | |
| *A61B 1/273* | (2006.01) | |
| *A61B 5/07* | (2006.01) | |
| *A61B 5/145* | (2006.01) | |
| *A61B 5/00* | (2006.01) | |

(Continued)

(52) U.S. Cl.
CPC .......... *A61B 1/041* (2013.01); *A61B 1/00082* (2013.01); *A61B 1/00156* (2013.01); *A61B 1/015* (2013.01); *A61B 1/273* (2013.01); *A61B 5/07* (2013.01); *A61B 5/073* (2013.01); *A61B 1/00009* (2013.01); *A61B 5/0084* (2013.01); *A61B 5/01* (2013.01); *A61B 5/036* (2013.01); *A61B 5/14539* (2013.01); *A61B 5/4839* (2013.01)

(58) Field of Classification Search
CPC ..... A61B 1/041; A61B 1/00082; A61B 1/015; A61B 1/12; A61B 1/273; A61B 1/2733; A61B 1/2736; A61B 1/31; A61B 1/00156; A61B 1/00158; A61B 1/01; A61M 29/00; A61M 29/02; A61M 31/00; A61M 31/002
See application file for complete search history.

(56) References Cited

U.S. PATENT DOCUMENTS

| | | | |
|---|---|---|---|
| 2005/0124875 A1* | 6/2005 | Kawano | A61B 1/00048 600/407 |
| 2008/0194912 A1* | 8/2008 | Trovato | A61B 1/00055 600/118 |

(Continued)

*Primary Examiner* — Ryan Henderson
(74) *Attorney, Agent, or Firm* — Knobbe Martens Olson & Bear LLP

(57) ABSTRACT

A closed-loop endoscopic capsule including a sensor recording biological information reflecting the inner condition of a gastrointestinal tract, an expander which is inflatable and holds the endoscopic capsule in the gastrointestinal tract, a medication releaser releasing medication for treatment, and a controller for processing the recorded biological information to generate control signals for the expander and the releaser. An endoscopic system that includes the endoscopic capsule, an external station for data processing, and a mobile device for human-machine interaction.

17 Claims, 12 Drawing Sheets

(51) Int. Cl.
*A61B 1/015* (2006.01)
*A61B 5/01* (2006.01)
*A61B 5/03* (2006.01)

(56) References Cited

U.S. PATENT DOCUMENTS

| | | | | |
|---|---|---|---|---|
| 2009/0281387 | A1* | 11/2009 | Takizawa | A61B 1/00082 600/117 |
| 2013/0138132 | A1* | 5/2013 | Phee | A61F 5/0046 606/192 |
| 2015/0045658 | A1* | 2/2015 | Tange | A61B 5/073 600/424 |

* cited by examiner

ENDOSCOPIC CAPSULE AND ENDOSCOPIC SYSTEM

RELATED APPLICATION

This application claims priority to U.S. Provisional Application No. 62/107,760, filed Jan. 26, 2015, the entire contents of which are incorporated herein by reference.

TECHNICAL FIELD

The present application generally relates to an endoscopic capsule and an endoscopic system comprising the same.

BACKGROUND

Nowadays, medical workers usually use endoscopy to perform screening and treatment of gastrointestinal (GI) tracts related diseases. This may involve the implantation of intrafluidtric balloon, observing and photographing tissue, taking biopsy, and the activation of hemostasis. In conventional method, an endoscopy is introduced into a patient through the mouth or colon. This procedure requires sedation, and could induce abdominal pain and distention to patients. Non-invasive treatments and investigation of the GI tracts can increase patients' willingness to undergo regular disease screening, enhance patients' clinical experience, and resolve the problem with patients discomfort during endoscopy examination. Recently, therapeutic wireless capsule endoscopy (WCE) system has been introduced to provide endoscopic images from the intestines for diagnosis and treatment for GI tracts related diseases, and therefore enabling the non-invasive examination of the GI tracts.

U.S. Pat. No. 8,852,083B2 discloses a self-stabilized encapsulated imaging system comprising a swallowable capsule and an expandable material attached to an end of the capsule. The expandable material is capable of swelling due to absorption of gastrointestinal fluid for stabilizing said capsule against tumbling in the gastrointestinal organ, while expansion of the expandable material can't be accurately controlled.

US 20050029437 A1 discloses a capsule optical sensor. The capsule optical sensor includes an illuminator producing light in the wavelength range from 600 to 2000 nm and the sensor has a photoelectric detection element and a variable spectroscopic element in front of a light receiving surface of the photoelectric detection element.

US 20050183733 A1 discloses a capsule type medical device system. The system includes an electrode on the surface of the capsule type medical and an expandable balloon for providing close contact between the electrode and living body tissues. However, the purpose of the electrode is to propel the capsule type medical device by applying electrical stimulus to living body tissues, and the expandable balloon can't be accurately controlled and can't provide enough force to anchor the capsule at a specific position.

US 20100137683 A1 discloses a capsule-type endoscope having sensor and communication method thereof. The capsule-type endoscope includes one or more sensors for obtaining information related to the inside of the body, the sensor can be pH sensor, temperature sensor, or pressure sensor. However, the capsule-type endoscope cannot determine the location of the capsule.

US 20110245604 A1 discloses a capsule endoscopy system. The system includes an external control system comprising a data acquisition module for acquainting images from an endoscopic capsule, a remote control module for sending the images from the data acquisition module to a display module. An electronic switch is integrated in the endoscopic capsule and the external control system can control the activation of the capsule remotely. However, the capsule cannot process image data and perform treatment by itself.

US 2011/0245611 A1 discloses an expandable capsule endoscope and expandable capsule endoscope system. The purpose of US 2011/0245611 A1 is to flatten the wrinkles and folds of the large intestine wall and to prevent random rotation of said capsule endoscope for better quality of image capturing. The expandable module is an inflatable balloon that is inflated by the reaction of two substances, while the inflating mechanism is a solenoid for opening a valve to expose one reaction substance to another reaction substance.

US 20120209083 A1 discloses a method of locating an ingested capsule. The ingestible capsule includes a pH sensor and a pressure sensor. The method involves recording pH measurements from the pH sensor and recording pressure measurements from the pressure sensor. However, the method requires both the recorded pH measurements and pressure measurements to determine the location.

CN 202843608U discloses a Bluetooth transponder system for capsule endoscope. The transponder system includes a Bluetooth module to communicate with a mobile phone and a portable recorder that can collect image from the capsule endoscope. The purpose of this invention is only to transmit images captured by the capsule endoscope to a mobile phone in real time.

US 2014/0135698A1 discloses a swallowable medication capsule for dispensing fluid medicine. This medication capsule includes a medication reservoir for the storage of medication, an actuator unit and a displaceable surface. The actuator unit can be a linear motor and the displaceable surface can be a piston. The purpose of this invention is only to propel medication out of the medication reservoir by a linear motor driven piston.

SUMMARY

The present invention discloses a standalone therapeutic wireless capsule endoscopy system for diagnosing and treating GI tracts related diseases such as digestive disorders. The system comprises an ingestible therapeutic wireless endoscopic capsule that could automatically diagnose and treat GI tracts related diseases in situ, an optional external station providing an additional human-machine interface for human physiological condition monitoring, capsule monitoring and control.

According to an aspect of the present application, disclosed is an endoscopic capsule. The endoscopic capsule comprises a sensor recording biological information of a gastrointestinal tract; an expander having an inflatable cavity, the inflatable cavity being inflatable by injecting fluid and deflatable by discharging the fluid therefrom; and a controller determining an affected part in the gastrointestinal tract from the recorded biological information, and controlling the expander to have: an inflation position, in which the inflatable cavity is inflated by injected fluid and the expander is, via the inflated cavity, held adjacent to the determined affected part in the gastrointestinal tract; or a deflation position, in which at least a portion of the injected fluid in the inflatable cavity is released and the expander retracts from the gastrointestinal tract.

In embodiments of the present application, the endoscopic capsule may further comprise a releaser comprising a medication chamber for receiving the medication to be released in the gastrointestinal tract.

In embodiments of the present application, the expander may further comprise: a housing having a first channel being fluidly communicated with the inflatable cavity, and a second channel; and a fluid tank having a fluid cavity for receiving compressed fluid, the fluid cavity being fluidly communicated with the inflatable cavity to inject the fluid into the inflatable cavity.

In embodiments of the present application, the fluid tank may comprise: comprises an electronically controlled valve controllable by the controller, to deliver the compressed fluid from the fluid cavity to the inflatable cavity or discharge the fluid from the inflatable cavity.

In embodiments of the present application, the expander may further comprise: a housing enclosing a first chamber and a second chamber and having a first channel being fluidly communicated with the first chamber and a second channel, wherein the first chamber stores base, and the second chamber stores acid and further comprises an end wall. The expander may have an inflation status in which the end wall is pushed forward to compress the second chamber such that the acid therein flows into the first chamber through the first channel and mixed with the base to generate the fluid to inflate the inflatable cavity to make the expander held adjacent to the determined affected part in the gastrointestinal tract and a deflation status in which the end wall is pulled backward beyond the second channel to let the fluid leak from the inflatable cavity to make the expander retract from the gastrointestinal tract.

In embodiments of the present application, the expander may comprise: an actuator engaged with the end wall for pushing and pulling the end wall.

In embodiments of the present application, the actuator may comprise: a driver providing a rotational displacement; a pair of gears engaged with each other, one of the gears being connected to the driver and transferring the rotational displacement to the other one of the gears; and a scissors linkage connected to the other gear and converting the rotational displacement to a linear displacement for pulling or pushing the end wall.

In embodiments of the present application, the actuator may further comprise a driver providing a rotational displacement; a pair of gears engaged with each other, one of the gears being connected to the driver and transferring the rotational displacement to the other one of the gears; and a lead screw and nut assembly connected to the other gear and converting the rotational displacement to a linear displacement for pulling or pushing the end wall.

In embodiments of the present application, the releaser may comprise a housing enclosing the medication chamber and having a releasing channel, wherein the medication chamber further comprises an end wall, which is pushed forward to release the medication through the releasing channel.

In embodiments of the present application, the releaser may comprise an actuator engaged with the end wall for pushing the end wall.

In embodiments of the present application, the actuator may comprise: a driver providing a rotational displacement; a pair of gears engaged with each other, one of the gears being connected to the driver and transferring the rotational displacement to the other one of the gears; and a scissors linkage connected to the other gear and converting the rotational displacement to a linear displacement for pushing the end wall.

In embodiments of the present application, the actuator may further comprise a driver providing a rotational displacement; a pair of gears engaged with each other, one of the gears being connected to the driver and transferring the rotational displacement to the other one of the gears; and a lead screw and nut assembly connected to the other gear and converting the rotational displacement to a linear displacement for pushing the end wall.

In embodiments of the present application, the actuator may be a fluid generating cell generating fluid to push the end wall.

In embodiments of the present application, the capsule comprises a shell having a sensor on the surface, and covering the internal sensor, the housing of the expander, the controller and the housing of the releaser.

According to an embodiment of the present application, disclosed is an endoscopic system. The system comprises an endoscopic capsule which comprises a sensor recording biological information of a gastrointestinal tract, a controller determining a location of the capsule and an affected part in the gastrointestinal tract from the recorded biological information, a releaser with a medication chamber for receiving the medication to be released in the gastrointestinal tract and an expander having an inflatable cavity. The expander may further have a housing enclosing a first chamber storing base and a second chamber storing acid and having a first channel fluidly communicated with the first chamber. The expander may have an inflation status in which the acid in the second chamber flows into the first chamber through the first channel and is mixed with the base to generate the fluid, the generated fluid is injected to and inflate the inflatable cavity, and the expander is, via the inflated cavity, held adjacent to the determined affected part in the gastrointestinal tract; and a deflation status in which the fluid leaks from the inflatable cavity and the expander retracts from the gastrointestinal tract.

In embodiments of the present application, the housing may have a second channel, and the second chamber may comprise an end wall. In the inflation status, the end wall may be pushed forward to compress the second chamber such that the acid therein flows into the first chamber through the first channel and is mixed with the base to generate the fluid to inflate the inflatable cavity such that the expander is held adjacent to the determined affected part. In the deflation status, the end wall may be pulled backward beyond the second channel to let the fluid leak from cavity such that the expander retracts from the gastrointestinal tract.

In embodiments of the present application, the actuator may comprise: a driver providing a rotational displacement; a pair of gears engaged with each other, one of the gears being connected to the driver and transferring the rotational displacement to the other one of the gears; and a scissors linkage connected to the other gear and converting the rotational displacement to a linear displacement for pushing and pulling the end wall.

In embodiments of the present application, the actuator may further comprise a driver providing a rotational displacement; a pair of gears engaged with each other, one of the gears being connected to the driver and transferring the rotational displacement to the other one of the gears; and a lead screw and nut assembly connected to the other gear and converting the rotational displacement to a linear displacement for pushing and pulling the end wall.

In embodiments of the present application, the releaser may further comprise a housing enclosing the medication chamber and having a releasing channel. The medication chamber may further comprise an end wall, which is pushed forward to release the medication through the releasing channel.

According to an embodiment of the present application, disclosed is a method for releasing medication in a gastrointestinal tract by an endoscopic capsule. The capsule comprises an expander and a controller. The method may comprises a) recording biological information of the gastrointestinal tract; b) determining an affected part or a desired location based on the recorded biological information; c) mixing acid and base to generate fluid in the expander; and d) injecting the generated fluid to the expander such that the expander is inflated by the injected fluid and held adjacent to the determined affected part in the gastrointestinal tract.

In embodiments of the present application, the expander may comprise a housing having a discharging channel and enclosing a first chamber for receiving base and a second chamber for receiving acid and comprising an end wall. The mixing may further comprise pushing the end wall forward to compress the second chamber such that the acid therein flows into the first chamber and is mixed with the base to generate the fluid.

In embodiments of the present application, the expander may further comprise an inflatable cavity being communicated with the first chamber. The injecting may further comprise injecting the generated fluid to the inflatable cavity to inflate such that the expander is, via the inflated cavity, held adjacent to the determined affected part in the gastrointestinal tract.

In embodiments of the present application, the method may comprise pulling the end wall backward beyond the second channel to let the fluid leak from cavity such that the expander retracts from the gastrointestinal tract.

In embodiments of the present application, the biological information may comprise at least one selected from a group consisting of 2-D or 3-D image data, temperature data, pH data, vascular blood flow data, and pressure data.

BRIEF DESCRIPTION OF THE DRAWING

Exemplary non-limiting embodiments of the present invention are described below with reference to the attached drawings. The drawings are illustrative and generally not to an exact scale. The same or similar elements on different figures are referenced with the same reference numbers.

DETAILED DESCRIPTION

Reference will now be made in detail to exemplary embodiments, examples of which are illustrated in the accompanying drawings. When appropriate, the same reference numbers are used throughout the drawings to refer to the same or like parts.

Figure 1:
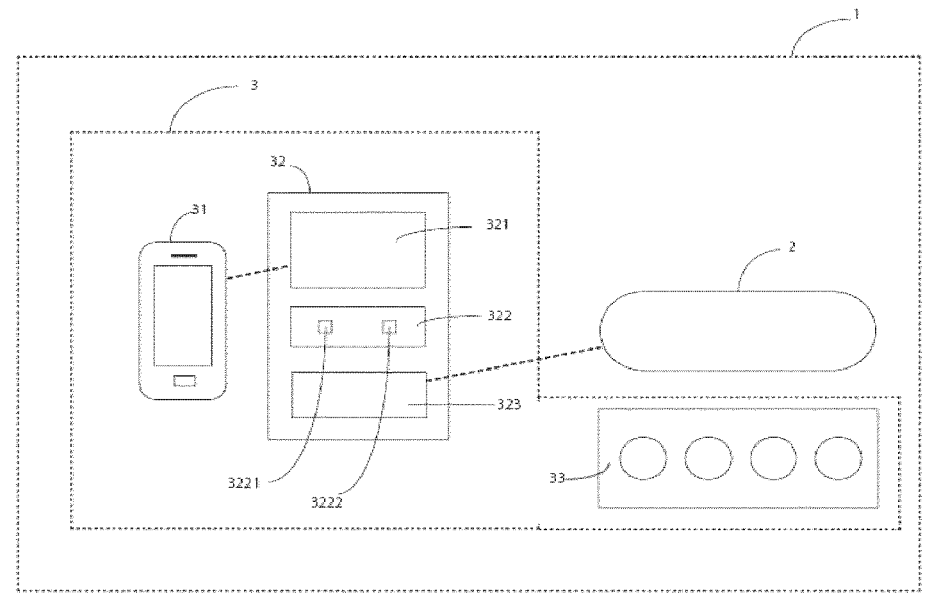
FIG. 1 is a schematic view of a therapeutic wireless capsule endoscopy system according to an embodiment of the present application.

FIG. 1 is a therapeutic wireless capsule endoscopy system according to an embodiment of the present application. In FIG. 1, a therapeutic wireless capsule endoscopy system 100 for diagnosis and treatment of GI tracts related diseases such as digestive disorders is illustrated.

Figure 2:
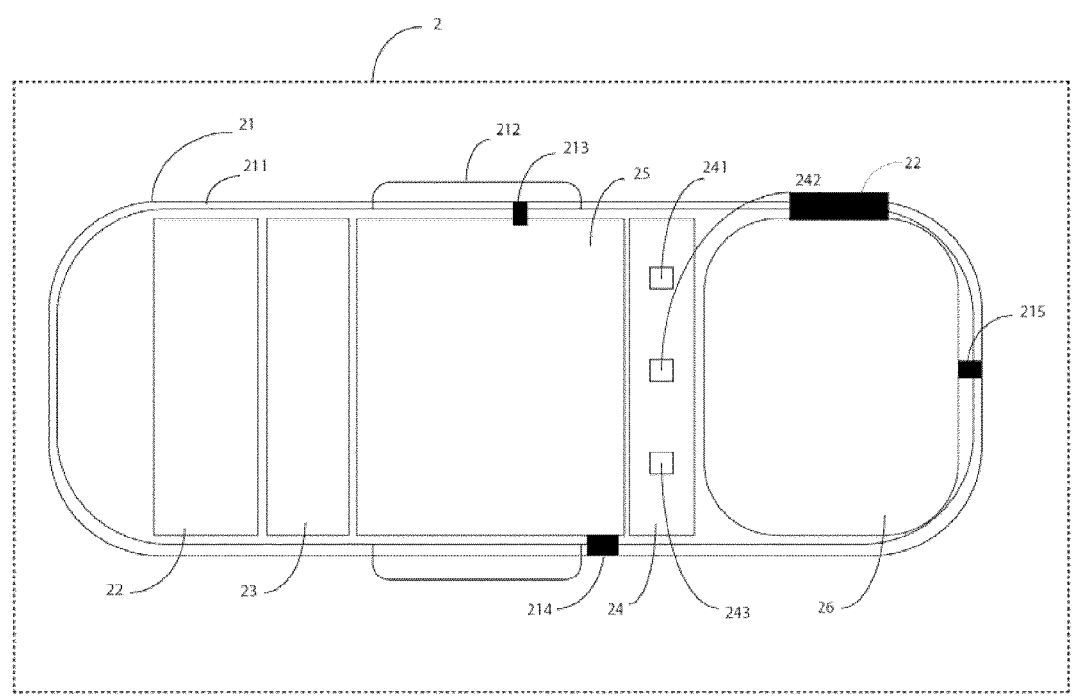
FIG. 2 is a schematic view of a one-segment design of the therapeutic wireless endoscopic capsule according to an embodiment of the present application.

The endoscopy system 100 includes at least one therapeutic wireless endoscopic capsule 2. FIG. 2 is a schematic view of a one-segment design of the therapeutic wireless endoscopic capsule 2 according to an embodiment of the present application. As shown in FIG. 2, the therapeutic wireless endoscopic capsule 2 may be an one-segment design, including a capsule body 21, a sensor 22, a battery 23, a data processing unit 24, an inflatable module control unit 25 and an additional treatment unit 26. The sensor 22 can be an imager, an optical sensor, or the like.

The capsule body 21 may include at least one piece of capsule shell 211, an inflatable module 212, at least one inflation fluid exit hole 213, at least one deflation fluid exit hole 214, at least one medication releasing exit hole 215, at least one sensor 216 (not shown). The capsule shell 211 is used for covering the sensor 22, the battery 23, the data processing unit 24, the inflatable module control unit 25 and the additional treatment unit 26 and can be made of flexible material like rubber, or the like. In some embodiment, the capsule shell 211 can be omitted. The inflatable module 212 may have a cavity being inflatable by injecting fluid through the inflation fluid exit hole 213. Once the fluid is injected into the cavity, the module 212 is inflated and enables the capsule 2 to be closely contact with the gastrointestinal tract or other position for subsequent treatment, or to provide a tamponade effect to stop gastrointestinal bleeding. The cavity is also deflatable by discharging the fluid through the deflation fluid exit hole 214. The inflatable module 212 can be made of any inflatable material. The sensor 216 can be a temperature sensor, a pH sensor, an optical sensor, a pressure sensor, or the like.

The sensor 22 may be located at an end of the capsule 2 to ensure that biological information downstream of the GI tract can be recorded regardless of an orientation of the capsule 2 in the GI tract. The sensor 22 may record biological information (e.g. images) reflecting the inner condition of gastrointestinal tract. The recorded biological information can be sent to the data processing unit 24 for data processing. The sensor 216 may be mounted on the surface of the capsule shell 211. The information collected by the sensor 216 can be temperature data measured by a temperature sensor, pH data measured by a pH sensor, or vascular blood flow data measured by an optical sensor, pressure data measured by a pressure sensor. The biological information recorded by the sensor 216 can be sent to the data processing unit 24 for location detecting.

The battery 23 may provide power supply for the capsule 2.

The data processing unit 24 is used for processing data, especially the biological information recorded by the sensor 22 and the sensor 216. The data processing unit 24 may be made of flexible PCB and includes a microcontroller 241, a wireless module 242, and a digital signal processor 243.

The microcontroller 241 controls the activation of all units in the capsule 2. In some embodiments, an algorithm for digestive disorder detection can be implemented in the microcontroller 241 to analyze the biological information recorded by the sensor 22. In some embodiments, an algorithm for digestive disorder detection can be implemented in the microcontroller 241 to analyze the information recorded by the sensor 216. In some embodiments, control signals can be received from the external station 3 and delivered to the microcontroller 241 to control the activation of all units in the capsule 2. The wireless module 242 is used for communication with other external devices such as the external station 3. For example, the biological information recorded by the sensor 22 and sensor 216 may be sent to the external station 3 via the wireless module 242 for monitoring. In some embodiments without external devices, the wireless module 242 can be omitted. An algorithm for digestive disorder detection may be implemented in the digital signal processor 243 to analyze the biological information recorded by the sensor 22. An algorithm for digestive disorder detection may be implemented in the digital signal processor 243 to analyze the biological information recorded by the sensor 216.

The inflatable module control unit 25 may be activated to generate fluid to inflate the inflatable module 212 through the inflation fluid exit hole 213. The fluid generated may be $CO_2$, or the like. Also, the inflatable module 212 can be deflated via the activation of the inflatable module control unit 25 letting fluid being leaked from the deflation fluid exit hole 214.

The treatment unit 26 is used for receiving and releasing medication 620, and may be activated to release medication 620 out of the capsule 2 through the medication releasing exit hole 215. The medication 620 can be fluid-like medication, fluid-like medication, powder-like medication, or the like. The treatment unit 26 may release medication for additional treatment in a predetermined condition.

Figure 3:
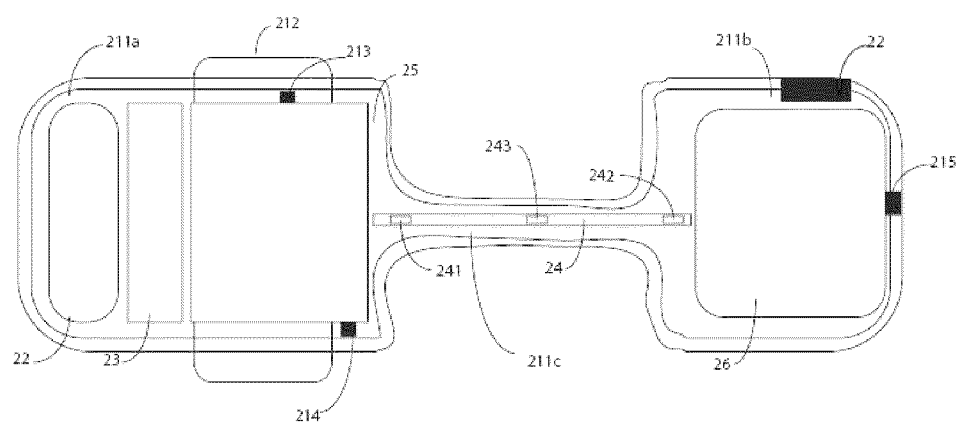
FIG. 3 is a schematic view of a multi-segment design of the therapeutic wireless endoscopic capsule with multiple segments according to an embodiment of the present application.

It is understood by those skill in the art that the therapeutic wireless endoscopic capsule should not be limited to the configuration shown in FIG. 2 and can have the configuration shown in FIG. 3 in which the capsule shell 211 can be divided into a first part 211a enclosing the sensor 22, the battery 23, and the inflatable module control unit 25, a second part 211b enclosing the additional treatment unit 26, and a third part 211c enclosing the data processing unit 24, respectively. The first part 211a and the second part 211b may be connected with the third shell 211c which can be made of flexible material like rubber, or the like.

Figure 4:
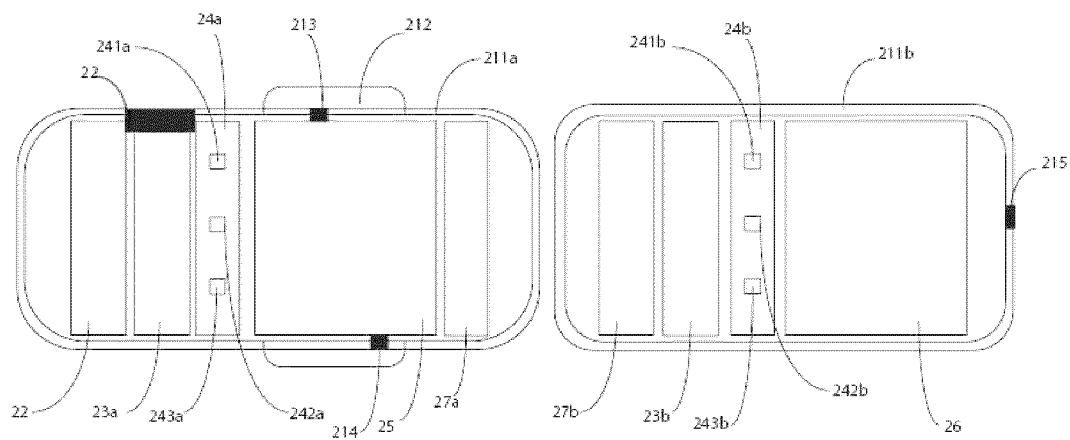
FIG. 4 is a schematic view of another multi-segment design of the therapeutic wireless endoscopic capsule with multiple segments according to another embodiment of the present application.

FIG. 4 is a schematic view of another multi-segment design of the therapeutic wireless endoscopic capsule with multiple segments according to another embodiment of the present application. As shown in FIG. 4, the therapeutic wireless endoscopic capsule 2' can be a multi-segment design, including a capsule 2a and a capsule 2b. The capsule 2a includes a capsule body 21a, a sensor 22', a battery 23a, a data processing unit 24a, an inflatable module control unit 25', and an RFID unit 27a. Meanwhile, the capsule 2b includes a capsule body 21b, an RFID unit 27b, a battery 23b, a data processing unit 24b, and a treatment unit 26'. With such a multi-segment design, the size of the capsule may be reduced such that those patients having dysphagia can swallow more easily.

The capsule body 21a includes at least one piece of capsule shell 211a, an inflatable module 212', at least one inflation fluid exit hole 213', at least one deflation fluid exit hole 214', at least one sensor 216'. The capsule body 21b includes at least one piece of capsule shell 211b, at least one medication releasing exit hole 215. The capsule shell 211a is used for covering the sensor 22', the battery 23a, the data processing unit 24a, the inflatable module control unit 25' and the RFID unit 27a, and the capsule shell 211b is used for covering the battery 23b, the data processing unit 24b, the additional treatment unit 26' and the RFID unit 27b. Both of the capsule shells 211a and 211b can be made of flexible material like rubber, or the like. In some embodiment, the capsule shells 211a and 211b can be omitted. The inflatable module 212' may have a cavity being inflatable by injecting fluid through the inflation fluid exit hole 213' to hold the capsule 2' in a position for subsequent treatment, or provide a tamponade effect to stop gastrointestinal bleeding, and being deflatable by discharging the fluid therefrom through the deflation fluid exit hole 214'. The inflatable module 212' can be made of any inflatable material. The sensor 216' can be a temperature sensor, a pH sensor, an optical sensor, a pressure sensor, or the like.

The sensor 22' may located at an end of the capsule to ensure biological information downstream of the GI tract can be recorded regardless of an orientation of the capsule in the GI tract. The sensor 22' can record biological information (e.g. images) reflecting the inner condition of gastrointestinal tract. The biological information recorded can be sent to the data processing unit 24a for image processing. The sensor 216' may be mounted on the surface of the capsule shell 211'. The information collected by the sensor 216' can be temperature data measured by a temperature sensor, pH data measured by a pH sensor, or vascular blood flow data measured by an optical sensor, pressure data measured by a pressure sensor. The biological information recorded by the sensor 216' can be sent to the data processing unit 24a for location detecting.

The batteries 23a and 23b may provide power supply for each segment of the capsule 2'.

The data processing unit 24a is used for processing data, especially the biological information recorded by the sensor 22' and the sensor 216'. The data processing unit 24a can be made of flexible PCB and includes a microcontroller 241a, a wireless module 242a, and a digital signal processor 243a. The data processing unit 24b can be made of flexible PCB and includes a microcontroller 241b, a wireless module 242b, and a digital signal processor 243b.

The microcontroller 241a controls the activation of all units in a first segment of the capsule 2', i.e., the sensor 22', the battery 23a, the data processing unit 24a, the inflatable module control unit 25', the RFID unit 27a. The microcontroller 241b controls the activation of all units in a second segment of the capsule 2', i.e., the battery 23b, the data processing unit 24b, the additional treatment unit 26' and the RFID unit 27b. In some embodiment, an algorithm for digestive disorder detection can be implemented in the microcontroller 241a to analyze the biological information recorded by the sensor 22'. In some embodiment, an algorithm for digestive disorder detection can be implemented in the microcontroller 241a to analyze the biological information recorded by the sensor 216'. In some embodiment, an algorithm for digestive disorder detection can be implemented in the microcontroller 241b to analyze the biological information recorded by the sensor 22'. In some embodiment, an algorithm for digestive disorder detection can be implemented in the microcontroller 241b to analyze the biological information recorded by the sensor 216'. In some embodiments, one of the microcontrollers 241a and 241b can be omitted. In some embodiments, control signals can be received from the external station 3 and delivered to the microcontroller 241a to control the activation of all units in the first segment of the capsule 2'. The wireless module 242a is used for communication with the wireless module 242b or other external devices such as the external station 3. For example, the biological information recorded by the sensor 22' and the biological information recorded by the sensor 216' may be sent to the external station 3 via the wireless module 242a for monitoring. In some embodiments without external devices, the wireless module 242a can be omitted. An algorithm for digestive disorder detection may be implemented in the digital signal processor 243a or 243b to analyze the biological information recorded by the sensor 22'. An algorithm for digestive disorder detection may be implemented in the digital signal processor 243a or 243b to analyze and the biological information recorded by the sensor 216'. In some embodiments, one of the digital signal processor 243a and 243b can be omitted.

The inflatable module control unit 25' may be activated to generate fluid to inflate the inflatable module 212' through the inflation fluid exit hole 213'. The fluid generated may be $CO_2$, or the like. Also, the inflatable module 212' can be deflated via the activation of the inflatable module control unit 25' letting fluid being leaked from the deflation fluid exit hole 214'.

The treatment unit 26' is used for receiving and releasing medication, and may be activated to release medication out of the capsule 2' through the medication releasing exit hole 215'. The medication can be fluid-like medication, fluid-like medication, powder-like medication, or the like. The treatment unit 26' may release medication for additional treatment in a predetermined condition.

Figure 5:
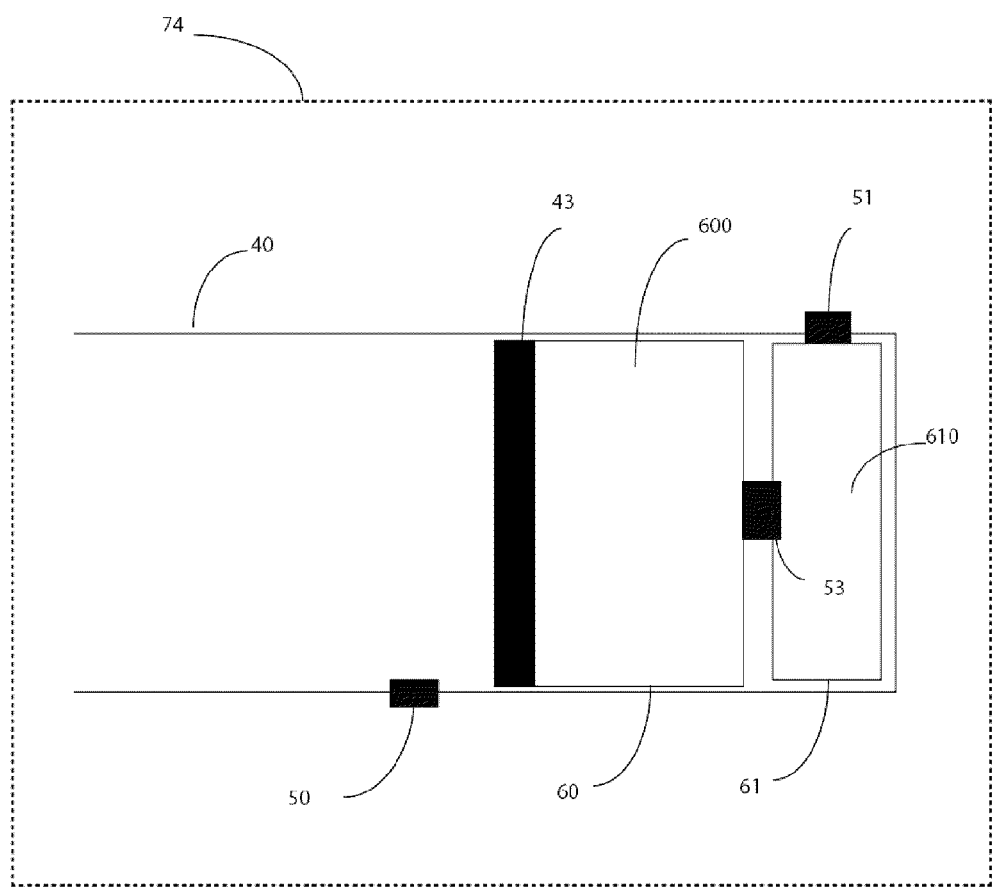
FIG. 5 is a schematic view of an acid and base unit according to an embodiment of the present application.

In some embodiments, the inflatable module control unit 25 or 25' may be an acid and base unit 74. FIG. 5 is a schematic view of the acid and base unit 74 according to an embodiment of the present application. The acid and base unit 74 includes a compartment body 40, an acid chamber 60 with acid 600 stored, a base chamber 61 with base 610 stored, at least one deflation fluid exit hole 50 fluidly communication with the deflation fluid exit hole 214/214', at least one inflation fluid exit hole 51 fluidly communication with the inflation fluid exit hole 213/213', and at least one chamber connection hole 53 fluidly communication the acid chamber 60 and the base chamber 61. The compartment body 40 is used to receiving or forming the acid chamber 60 and the base chamber 61 and can be a syringe, a bag, or the like. The acid 600 can be acetic acid, hydrochloric acid, or the like. The base 610 can be sodium bicarbonate, or the like. The acid chamber 60 may comprises an end wall i.e., the displaceable surface 43, which can be pushed forward to compress the acid chamber 60 such that the acid therein flows into the base chamber 61 and mixed with the base to generate the fluid passing through the inflation fluid exit hole 51 during the inflation and can be pulled backward beyond the deflation fluid exit hole 50 to let the fluid leak during the deflation. The displaceable surface 43 can be a piston, or the like.

Figure 6:
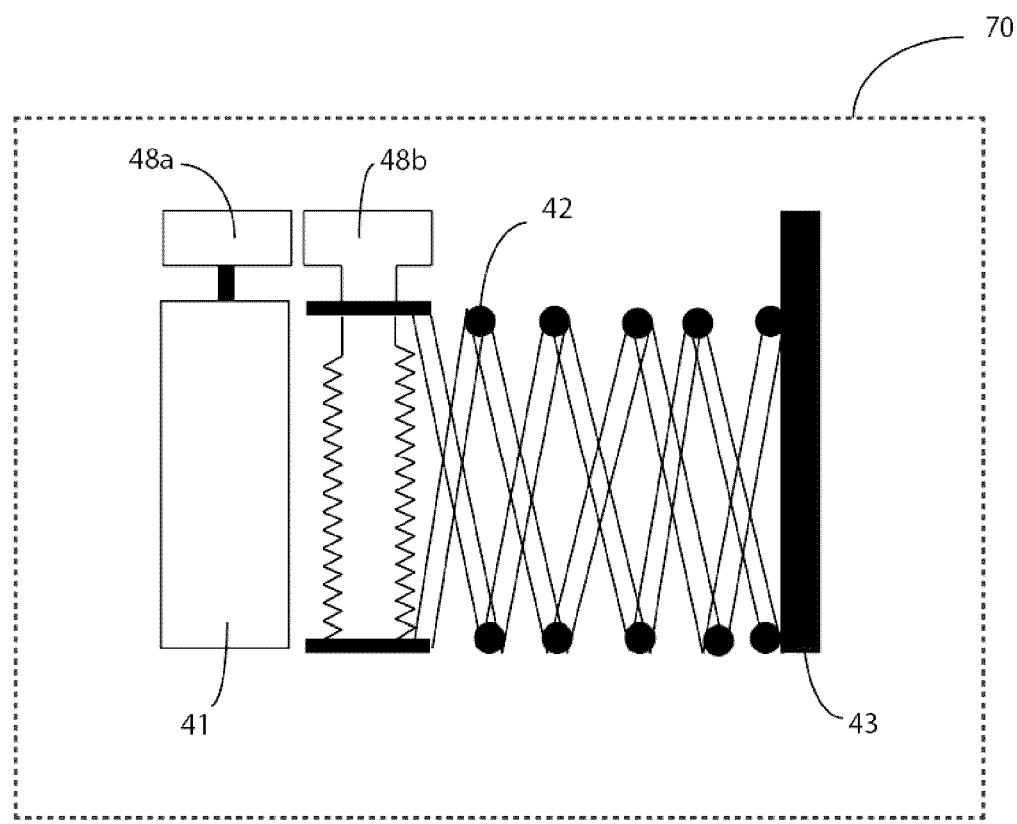
FIG. 6 is a schematic view of a displaceable surface driven mechanism with a scissors linkage according to an embodiment of the present application.

In some embodiment, a displaceable surface driven mechanism with a scissors linkage can combine with the acid and base unit 74 together as an inflatable module control unit 25 or 25'. Particularly, the displaceable surface 43 of the acid chamber 60 can be actuated by the displaceable surface driven mechanism 70 shown in FIG. 6. As shown in FIG. 6, the displaceable surface driven mechanism 70 with a scissors linkage may include a driver 41, such as a motor, providing a rotation displacement, a pair of gears 48a, 48b engaged with each other and transferring the rotational displacement from one gear 48a connected to the driver 41 to the other gear 48b, a scissors linkage 42 connected to the other gear 48a and converting the rotational displacement to a linear displacement for pulling or pushing a displaceable surface 43. With above displaceable surface driven mechanism, the acid 600 can be pushed out of acid chamber 60 by the displaceable surface 43 actuated by the mechanism 70 moving towards the base chamber 61 and mixes with base 610 to generate fluid for the inflation of the inflatable module 212 or 212'. Fluid can be leaked from the inflatable module 212 or 212' so that the inflatable module 212 or 212' can be deflated via the channel created by the deflation fluid exit hole 50 and the deflation fluid exit hole 214 or 214' with the inflatable module 212 or 212' when the displaceable surface 43 is pulled backwards and passed the fluid exit hole 50.

Figure 7:
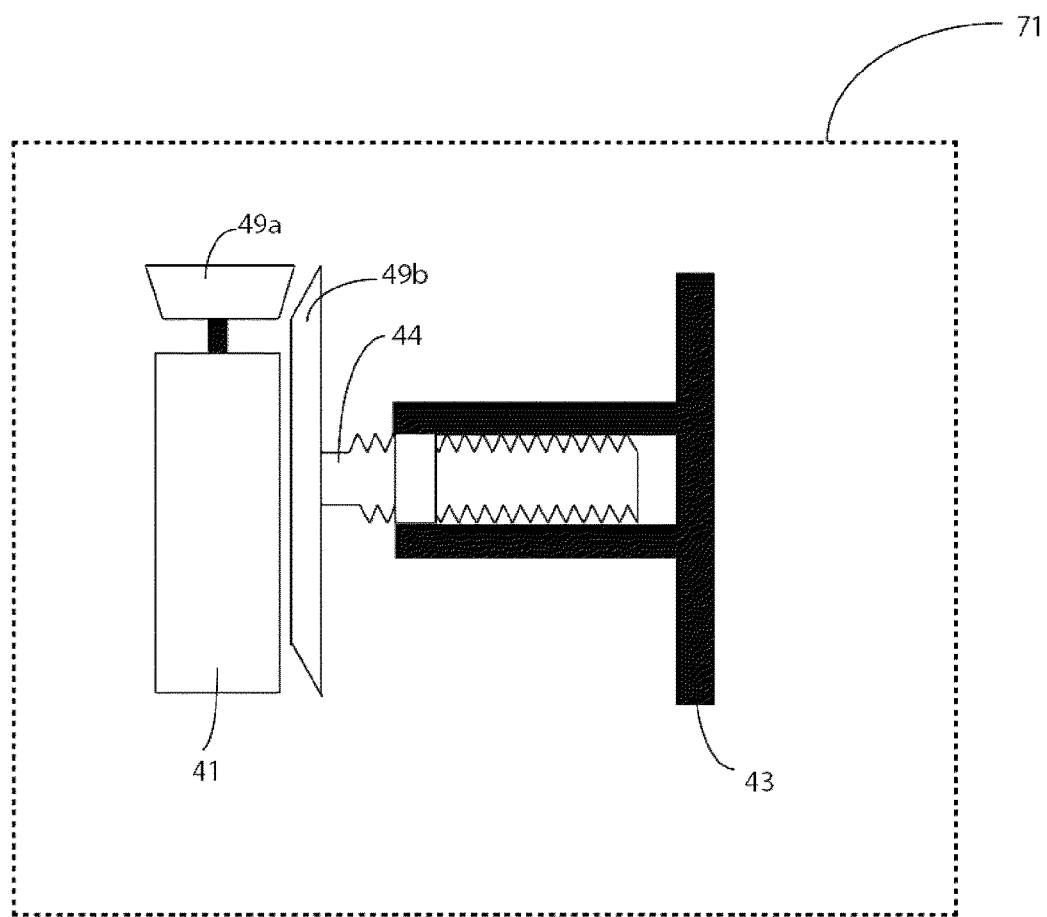
FIG. 7 is a schematic side view of a displaceable surface driven mechanism with a lead screw and nut assembly according to an embodiment of the present application.

In some embodiment, a displaceable surface driven mechanism with a lead screw and nut assembly can combine with the acid and base unit 74 together as an inflatable module control unit 25 or 25'. Particularly, the displaceable surface 43 of the acid chamber 60 can be actuated by the displaceable surface driven mechanism 71 shown in FIG. 7. As shown in FIG. 7, the displaceable surface driven mechanism 71 with a lead screw and nut assembly includes a driver 41, a gear pair 49a, 49b, and a lead screw and nut assembly 44. The driver 41 can be a motor, or the like. The driver 41 can transfer force from gear 49a to gear 49b to drive the lead screw and nut actuator 44 to pull and push the displaceable surface 43. With above displaceable surface driven mechanism, the acid 600 can be pushed out of acid chamber 60 by the displaceable surface 43 actuated by the mechanism 70 moving towards the base chamber 61 and mixes with base 610 to generate fluid for the inflation of the inflatable module 212 or 212'. Fluid can be leaked from the inflatable module 212 or 212' so that the inflatable module 212 or 212' can be deflated via the channel created by the deflation fluid exit hole 50 and the deflation fluid exit hole 214 or 214' with the inflatable module 212 or 212' when the displaceable surface 43 is pulled backwards and passed the fluid exit hole 50.

Figure 8:
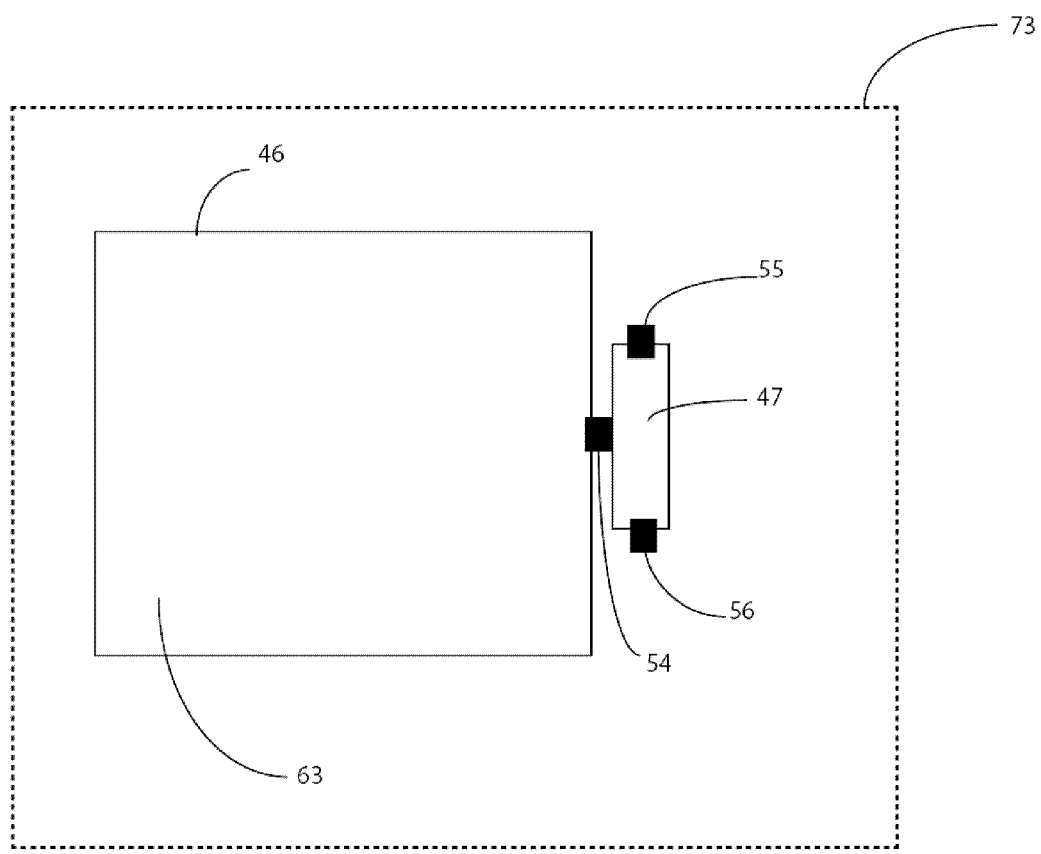
FIG. 8 is a schematic view of a fluid control mechanism with a compressed fluid tank according to an embodiment of the present application.

In some embodiment, the inflatable module control unit 25 or 25' may comprise a fluid control mechanism 73 shown in FIG. 8. The fluid control mechanism 73 includes a compressed fluid tank 46 with compressed fluid 63 stored therein, and an electronically operated valve 47. The electronically operated valve 47 includes at least one fluid tank connection joint 54, at least one inflation fluid exit joint 55, and at least one deflation fluid exit joint 56. The mechanism 73 can be used as an inflatable module control unit 25 or 25' with the inflation fluid exit joint 55 connected to inflation fluid exit hole 213, the deflation fluid exit joint 56 connected to deflation fluid exit hole 214. The compressed fluid 63 can be delivered to and inflate the inflatable module 212 by electronically opening of the inflation fluid exit joint 55. The inflatable module 212 can be deflated by electronically opening of the deflation fluid exit joint 56.

Figure 9:
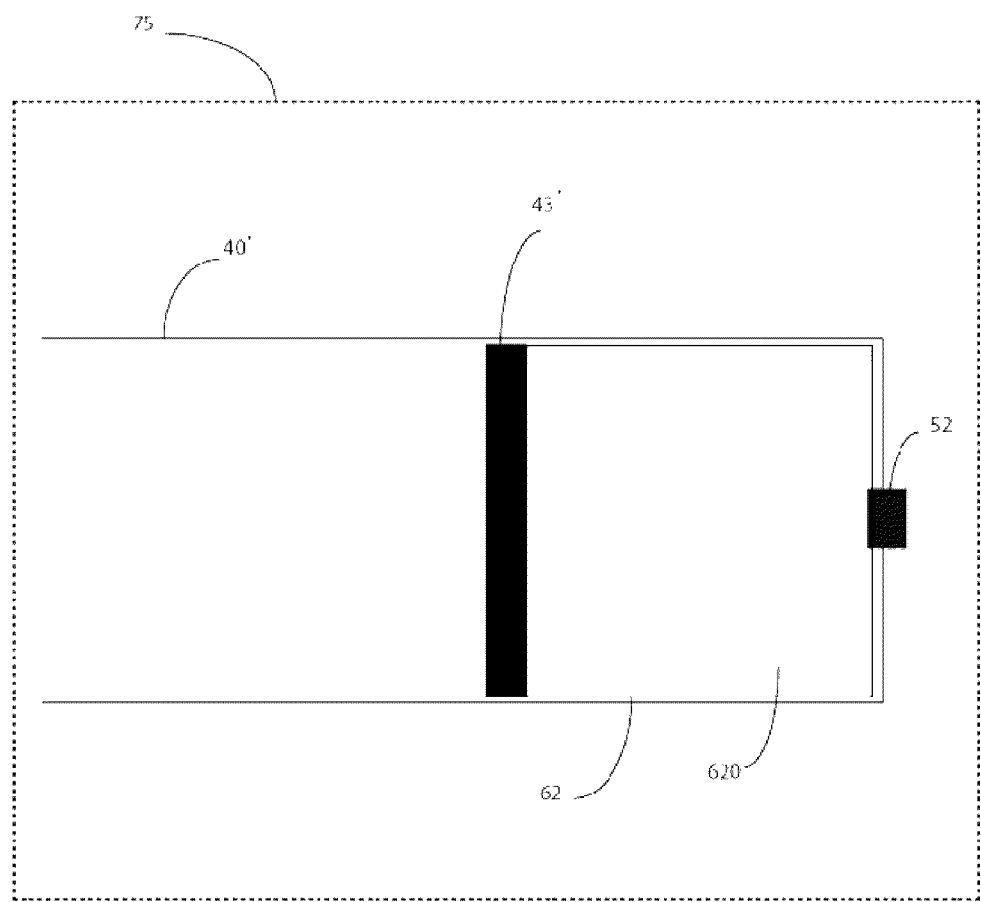
FIG. 9 is a schematic view of a medication unit according to an embodiment of the present application.

In some embodiments, the additional treatment unit 26 or 26' may be a medication unit 75. FIG. 9 is a schematic view of a medication unit 75 according to an embodiment of the present application. The medication unit 75 includes a compartment body 40', a medication chamber 62 with medication 620 stored, and at least one medication exit hole 52 fluidly communication with the medication releasing exit hole 215 or 215'. The compartment body 40' is used to receiving or forming medication chamber 62 and can be a syringe, a bag, or the like. The medication 620 can be fluid-like medication, fluid-like medication, powder-like medication, or the like. The medication chamber 62 may comprise an end wall, i.e., the displaceable surface 43', which can be pushed forward to compress the medication chamber 62 such that the medication therein flows out during the treatment. The displaceable surface 43' can be a piston, or the like.

Figure 10:
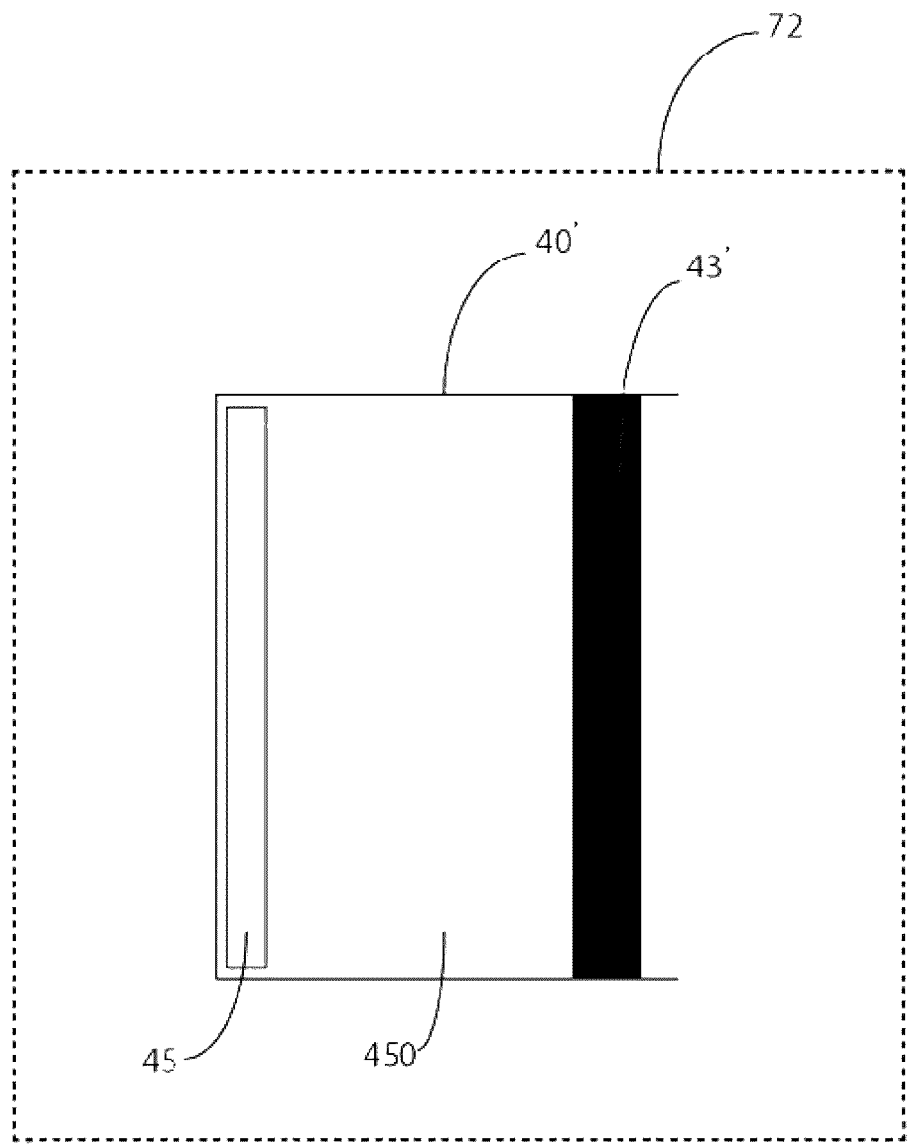
FIG. 10 is a schematic view of a displaceable surface driven mechanism with a fluid generating cell according to an embodiment of the present application.

In some embodiment, a displaceable surface driven mechanism with a fluid generating cell can combine with the medication unit 75 together as the additional treatment unit 26 or 26'. Particularly, the displaceable surface 43' of the medication chamber 62 can be actuated by the displaceable surface driven mechanism 72 shown in FIG. 10. The displaceable surface driven mechanism 72 includes a fluid generating cell 45 for generating fluid 450. The fluid 450 can be $CO_2$, or the like. The fluid 450 can push the displaceable surface 43'.

In some embodiment, the displaceable surface mechanisms 70 or 71 can also combine with the medication chamber 62 together as an additional treatment unit 26 or 26' with the medication exit hole 52 connected to the medication releasing exit hole 215. Medication 620 can be propelled out of the medication chamber 62 by the displaceable surface 43' actuated by the mechanisms 70 or 71 moving towards the medication exit hole 52.

Returning to FIG. 1, the endoscopy system 100 may include an external station 3 providing a human-machine interface between the capsule 2 and a user for monitoring and control of the endoscopic capsule.

In some embodiment, the external station 3 may includes a mobile device 31 providing a human-machine interface, a transponder 32 providing interchange of data between the mobile device 31 and the capsule 2, a set of sensors 33 for monitoring physiological condition of human, and optionally, an additional resource for data processing.

In some embodiment, the mobile device 31 may be a mobile phone, or the like. The transponder 32 may include a wireless module 321 for wireless communication between the mobile drive 31 and the transponder 32. The wireless module 321 can be a Bluetooth module, a Wi-Fi module, or the like. The mobile device 31 further comprises a wireless module 323 for wireless communication between the transponder 32 and the capsule 2. The wireless module 323 may be a RF module with bandwidth of 400-600 MHz, or the like. As shown, the mobile device 31 further comprises a data processing unit 322 including a microcontroller 3221 for the control of the transponder 32 and one digital signal processor 3222 for the additional resource for data processing. An algorithm for digestive disorder detection may be implemented in the digital signal processor 3222. The set of sensors 33 may be at least one electrode recording physiological information (e.g. ECG, EMG, or the like), or an optical sensor for measuring photoplethysmogram, or parameters calculated from the recorded physiological information or the like.

Data can be transmitted from the capsule 2 and the set of sensors 33 to the mobile device 31 via transponder 32 in a way of data first being transmitted from the capsule 2 to the wireless module 323, then delivered from the wireless module 323 to the wireless module 321, and further transmitted from the wireless module 321 to the mobile device 31. In some embodiment, the data may be delivered from the wireless module 323 to the digital signal processor 3222 for additional data processing before the transmission from the wireless module 323 to the wireless module 321.

In some embodiment, the mobile device 31 may control the capsule 2 by transmitting control signals to the transponder 32. To be specific, the control signal may be transmitted from the mobile device 31 to the wireless module 321 first, then be delivered from the wireless module 321 to the wireless module 323, and further be transmitted from the wireless module 323 to the capsule 2. The microcontroller 3221 controls the activation of the wireless module 321, the wireless module 323 and is responsible for the delivery of data in the transponder 32.

Figure 11:
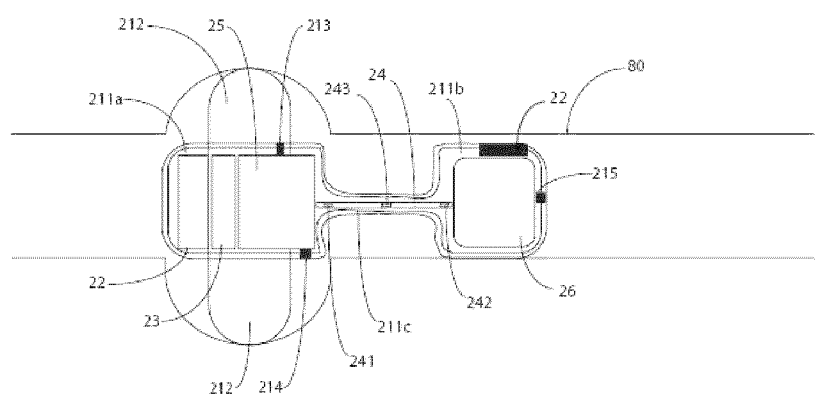
FIG. 11 is a schematic view of a multi-segment design of the therapeutic wireless endoscopic capsule holding at a position according to an embodiment of the present application.
Figure 12:
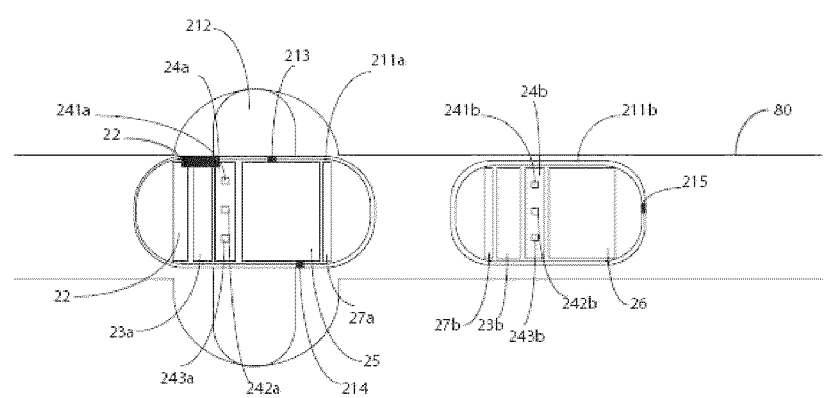
FIG. 12 is another multi-segment design of the therapeutic wireless endoscopic capsule holding at a position according to another embodiment of the present application.

FIG. 11 is a schematic view of a multi-segment design of the therapeutic wireless endoscopic capsule holding at a position according to one embodiment of the present application. FIG. 12 is another multi-segment design of the therapeutic wireless endoscopic capsule holding at a position according to another embodiment of the present application.

The therapeutic wireless capsule endoscopy system 1 can provide close-loop solution for diagnosis and treatment of GI tracts related diseases such as digestive disorder with or without the external station 3. The therapeutic wireless endoscopic capsule 2 will be swallowed and starts screening for digestive disorder in gastrointestinal tracts 80 according to FIG. 11. The therapeutic wireless endoscopic capsule 2a will be swallowed and starts screening for digestive disorder in gastrointestinal tracts 80 according to FIG. 12, the therapeutic wireless endoscopic capsule 2b will be swallowed a certain amount of time later than capsule 2a. Once digestive disorder is detected, the inflatable module 212 will be inflated to hold the capsule 2 according to FIG. 11 or capsule 2a according to FIG. 12 in a position and provide tamponade effect treatment for gastrointestinal bleeding in the meantime. Then additional treatment compartment 26 in capsule 2 according to FIG. 11 or capsule 2b according to FIG. 12 will be activated providing additional treatment. Data may be sent out from capsule 2 according to FIG. 11 or capsule 2a according to FIG. 12 to external station 3 for analysis throughout the whole process. Control signal may be sent out from external station 3 to control capsule 2 according to FIG. 11 or capsule 2a and capsule 2b according to FIG. 12. In some embodiment, a mobile phone can play the role of the external station since it is fully able to perform wireless communication and data processing.

Figure 13:
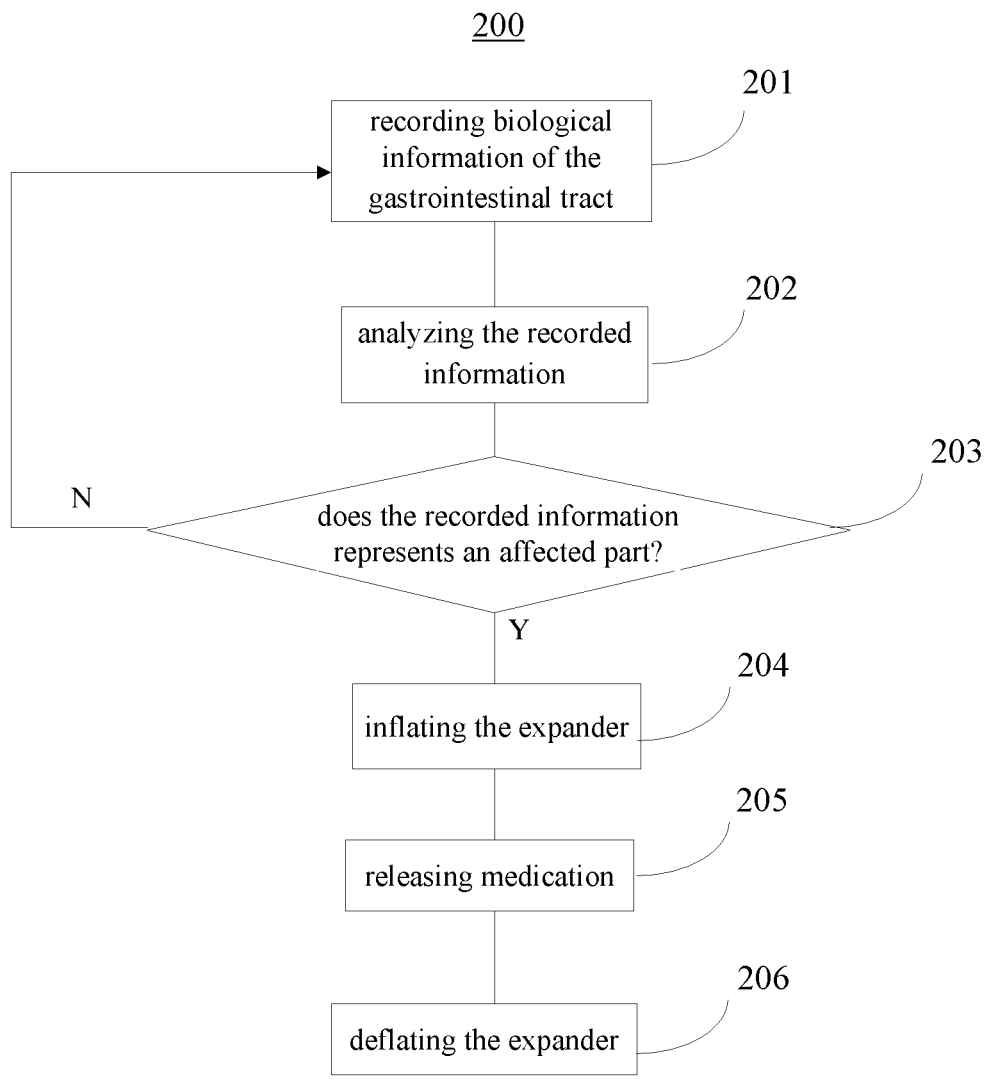
FIG. 13 is a flow chart of a method for releasing medication in a gastrointestinal tract by an endoscopic capsule according to an embodiment of the present application.

FIG. 13 is a flow chart of a method 200 for releasing medication in a gastrointestinal tract by the endoscopic capsule in above embodiments. The method comprises following steps. At step 201, an image of the gastrointestinal tract is capturing by the image capturing unit and sending to the data processing unit. At step 202, the recorded biological information are analyzed by the data processing unit. At step 203, whether the captured image represents an affected part is determined, if the captured image doesn't represents an affected part, the method goes back to step 201 to continue image capturing. Otherwise, the method goes to step 204 in which the inflatable module is inflated to hold it in the gastrointestinal tract. At step 205, medication is released by the releaser. After releasing, the method goes to step 206 in which the inflatable module is deflated to let it retract from the gastrointestinal tract.

Compared with traditional endoscopy use and currently available WCE, the disclosed solution in the present application provides a non-invasive solution for diagnosis and treatment of digestive disorders using a therapeutic wireless endoscopic capsule. In some embodiments of the present application, a digestive disorder detection algorithm may be implemented in the therapeutic wireless endoscopic capsule, and may be implemented in the external station as well. The capsule provides at least two treatment mechanisms, one is by tamponade effect and the other one is by medication delivery.

Although the preferred examples of the present invention have been described, those skilled in the art can make variations or modifications to these examples upon knowing the basic inventive concept. The appended claims is intended to be considered as comprising the preferred examples and all the variations or modifications fell into the scope of the present invention.

Obviously, those skilled in the art can make variations or modifications to the present invention without departing the spirit and scope of the present invention. As such, if these variations or modifications belong to the scope of the claims and equivalent technique, they may also fall into the scope of the present invention.

What is claimed is:

1. An endoscopic capsule comprising:
   a sensor for recording biological information inside a gastrointestinal tract;
   an expander having an inflatable cavity, the inflatable cavity being inflatable by injecting fluid and deflatable by discharging the fluid therefrom; and
   a controller determining an affected part in the gastrointestinal tract from the recorded biological information, and controlling the expander to have:
   an inflation position, in which the inflatable cavity is inflated by injected fluid and the expander is, via the inflated inflatable cavity, held adjacent to the determined affected part in the gastrointestinal tract; or
   a deflation position, in which at least a portion of the injected fluid in the inflatable cavity is released and the expander retracts from the gastrointestinal tract
   wherein the controller comprises:
   a base chamber separated from the inflatable cavity and communicated with the inflatable cavity via an inflation fluid exit hole, the base chamber storing base; and
   an acid chamber separated from the inflatable cavity and the base chamber, and communicated with the base chamber via a chamber connection hole, the acid chamber storing acid and comprising an end wall,
   wherein in the inflation position, the end wall is pushed forward to compress the acid chamber such that the acid flows from the acid chamber into the base chamber through the chamber connection hole and is mixed with the base to generate the fluid to inflate the inflatable cavity, and
   wherein in the deflation position, the end wall is pulled backward beyond a deflation fluid exit hole to let the fluid leak from the inflatable cavity.

2. The endoscopic capsule of claim 1, further comprising a releaser comprising a medication chamber for receiving a medication to be released in the gastrointestinal tract.

3. The endoscopic capsule of claim 1, wherein the controller further comprises an actuator engaged with the end wall for pushing and pulling the end wall.

4. The endoscopic capsule of claim 3, wherein the actuator comprises:
   a driver providing a rotational displacement;
   a pair of gears engaged with each other, one of the gears being connected to the driver and transferring the rotational displacement to the other one of the gears; and
   a scissors linkage connected to the other gear and converting the rotational displacement to a linear displacement for pulling or pushing the end wall.

5. The endoscopic capsule of claim 3, wherein the actuator comprises:
   a driver providing a rotational displacement;
   a pair of gears engaged with each other, one of the gears being connected to the driver and transferring the rotational displacement to the other one of the gears; and
   a lead screw and nut assembly connected to the other gear and converting the rotational displacement to a linear displacement for pulling or pushing the end wall.

6. The endoscopic capsule of claim 2, wherein the releaser further comprises a housing enclosing the medication chamber and having a releasing channel, wherein the medication chamber further comprises an end wall, which is pushed forward to release the medication through the releasing channel.

7. The endoscopic capsule of claim 6, wherein the releaser further comprises an actuator engaged with the end wall for pushing the end wall.

8. The endoscopic capsule of claim 7, wherein the actuator comprises:
   a driver providing a rotational displacement;
   a pair of gears engaged with each other, one of the gears being connected to the driver and transferring the rotational displacement to the other one of the gears; and
   a scissors linkage connected to the other gear and converting the rotational displacement to a linear displacement for pushing the end wall.

9. The endoscopic capsule of claim 7, wherein the actuator comprises:
   a driver providing a rotational displacement;
   a pair of gears engaged with each other, one of the gears being connected to the driver and transferring the rotational displacement to the other one of the gears; and
   a lead screw and nut assembly connected to the other gear and converting the rotational displacement to a linear displacement for pushing the end wall.

10. The endoscopic capsule of claim 6, wherein the actuator comprises a fluid generating cell generating fluid to push the end wall.

11. The endoscopic capsule of claim 2, further comprising a first shell covering the sensor, the housing of the expander and the controller, and a second shell covering the releaser.

12. The endoscopic capsule of claim 1, wherein the sensor is one selected from a group consisting of a 2-D or 3-D imaging sensor, a temperature sensor, a pH sensor, an optical sensor and a pressure sensor.

13. An endoscopic system having an endoscopic capsule, comprising:
   a sensor for recording biological information;
   a controller determining an affected part in a gastrointestinal tract from the recorded biological information;
   a releaser with a medication chamber for receiving a medication to be released in the gastrointestinal tract;
   an expander having an inflatable cavity and a housing enclosing:
      a first chamber storing base, wherein the first chamber is separated from the inflatable cavity and communicated therewith via an inflation fluid exit hole; and
      a second chamber storing acid, wherein the second chamber is separated from the inflatable cavity and the first chamber, and communicated with the first chamber via a chamber connection hole,
   wherein the expander comprises:
      an inflation status in which the acid in the second chamber flows into the first chamber through the chamber connection hole and is mixed with the base to generate the fluid, the generated fluid is injected into the inflatable cavity to inflate the inflatable cavity, and the expander is, via the inflated cavity, held adjacent to the determined affected part in the gastrointestinal tract; and
      a deflation status in which the fluid leaks from the inflatable cavity and the expander retracts from the gastrointestinal tract,
   wherein the housing has a deflation fluid exit hole, and the second chamber comprises an end wall;
   in the inflation status, the end wall is pushed forward to compress the second chamber such that the acid therein flows into the first chamber through the chamber connection hole and is mixed with the base to generate the fluid to inflate the inflatable cavity such that the expander is held adjacent to the determined affected part; and
   in the deflation status, the end wall is pulled backward beyond the deflation fluid exit hole to let the fluid leak from cavity.

14. The endoscopic system of claim 13, wherein the expander further comprises an actuator engaged with the end wall for pushing and pulling the end wall.

15. The endoscopic system of claim 14, wherein the actuator comprises:
   a driver providing a rotational displacement;
   a pair of gears engaged with each other, one of the gears being connected to the driver and transferring the rotational displacement to the other one of the gears; and
   a scissors linkage connected to the other gear and converting the rotational displacement to a linear displacement for pulling or pushing the end wall.

16. The endoscopic system of claim 14, wherein the actuator comprises:
   a driver providing a rotational displacement;
   a pair of gears engaged with each other, one of the gears being connected to the driver and transferring the rotational displacement to the other one of the gears; and
   a lead screw and nut assembly connected to the other gear and converting the rotational displacement to a linear displacement for pulling or pushing the end wall.

17. The endoscopic system of claim 13, wherein the releaser further comprises:
   a housing enclosing the medication chamber and having a releasing channel; and
   wherein the medication chamber further comprises an end wall, which is pushed forward to release the medication through the releasing channel.

* * * * *